United States Patent [19]

Takayama et al.

[11] Patent Number: 4,899,731
[45] Date of Patent: Feb. 13, 1990

[54] ENDOSCOPE

[75] Inventors: Syuichi Takayama, Hachioji; Yasuhiro Ueda, Kokubunji, both of Japan

[73] Assignee: Olympus Optical Co., Ltd., Tokyo, Japan

[21] Appl. No.: 289,538

[22] Filed: Dec. 23, 1988

Related U.S. Application Data

[63] Continuation of Ser. No. 106,248, Oct. 7, 1987, abandoned.

[30] Foreign Application Priority Data

Oct. 16, 1986 [JP] Japan ................................ 61-245773
Oct. 30, 1986 [JP] Japan ................................ 61-258856
Nov. 19, 1986 [JP] Japan ................................ 61-2760089

[51] Int. Cl.$^4$ ................................ A61B 1/00
[52] U.S. Cl. ................................ 128/4; 128/6; 358/98
[58] Field of Search ................................ 128/4, 6; 358/98

[56] References Cited

U.S. PATENT DOCUMENTS

| | | |
|---|---|---|
| 4,273,111 | 6/1981 | Tsukaya ................................ 128/6 |
| 4,286,585 | 9/1981 | Ogawa . | |
| 4,499,895 | 2/1985 | Takayama ................................ 128/6 |
| 4,503,842 | 3/1985 | Takayama . | |
| 4,559,928 | 12/1985 | Takayama . | |
| 4,601,283 | 7/1986 | Chikama ................................ 128/4 |
| 4,742,817 | 5/1988 | Kawashima et al. . | |
| 4,753,223 | 6/1988 | Bremer ................................ 128/4 |

FOREIGN PATENT DOCUMENTS

| | | |
|---|---|---|
| 2951764C2 | of 1982 | Fed. Rep. of Germany . |
| 58-25140 | 2/1983 | Japan . |
| 60-106601 | 7/1985 | Japan . |
| 60-217326 | 10/1985 | Japan ................................ 350/96.26 |
| 61-79439 | 4/1986 | Japan . |

Primary Examiner—Edward M. Coven
Assistant Examiner—Jessica Harrison
Attorney, Agent, or Firm—Frishauf, Holtz, Goodman & Woodward

[57] ABSTRACT

An endoscope disclosed herein is provided with an operating section and an insertion section having a bending section. Bending members, which are formed of a shape memorizable alloy and are for bending the bending section, are disposed within the bending section of the insertion section and are connected to a power supply unit. This endoscope further comprises a detecting unit for detecting the amount of deformation of the bending members as a change in electric resistance, and a display device for displaying the detected amount of deformation of the bending members. Accordingly, the bending amount of the bending section can accurately be detected and displayed.

6 Claims, 11 Drawing Sheets

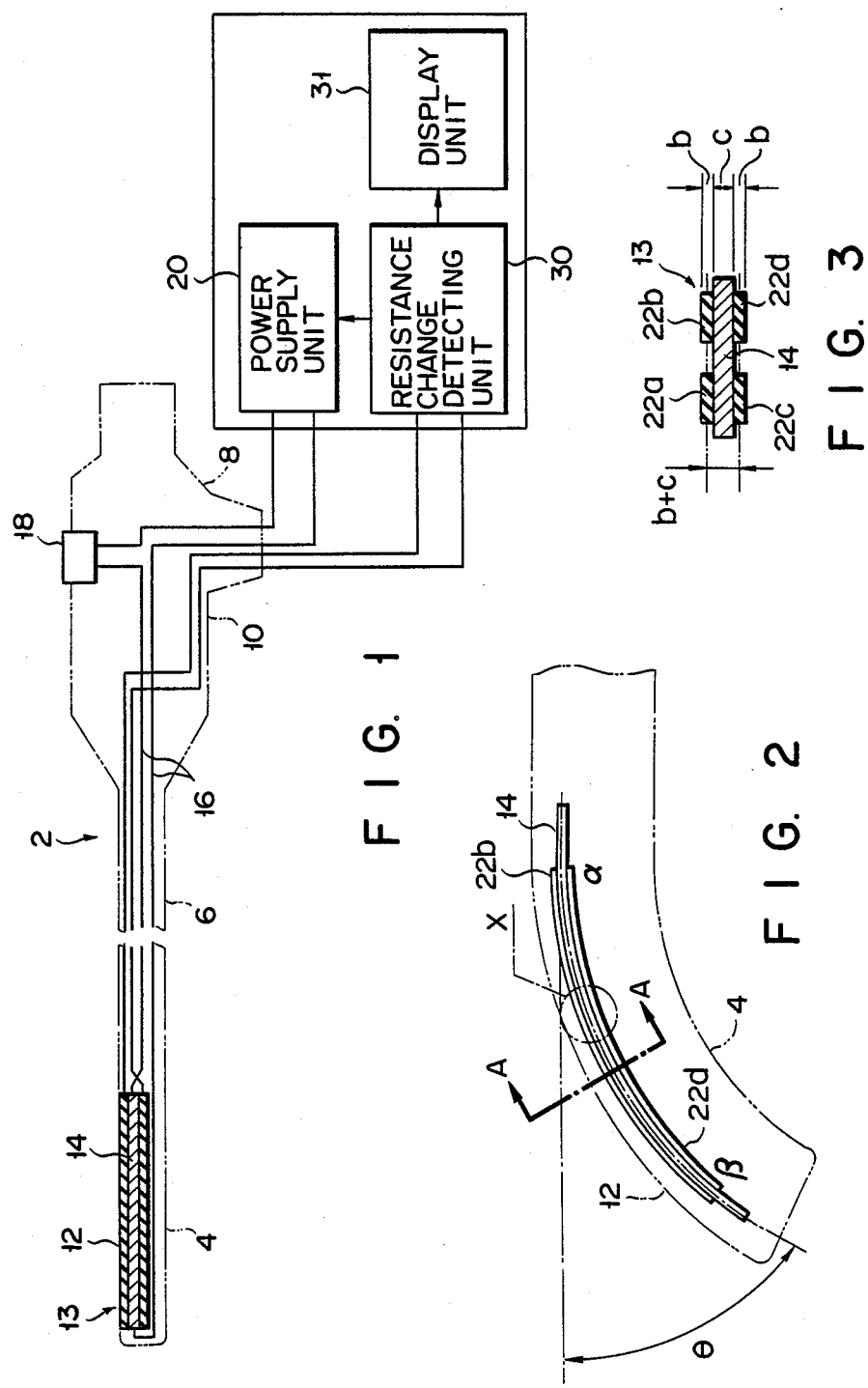

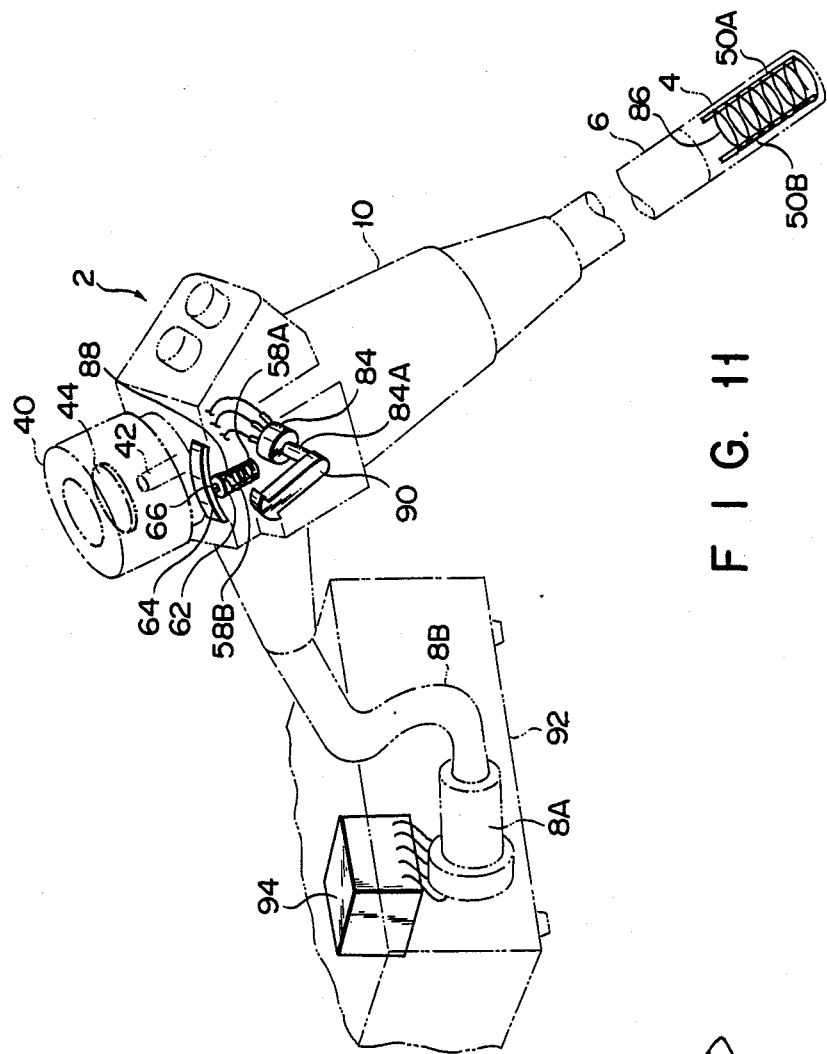
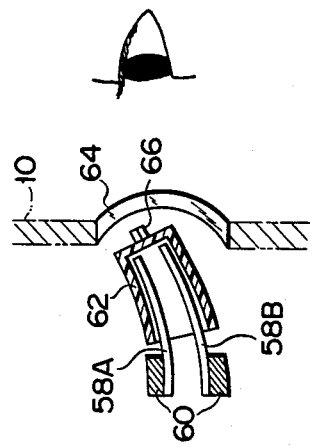
FIG. 11
FIG. 10

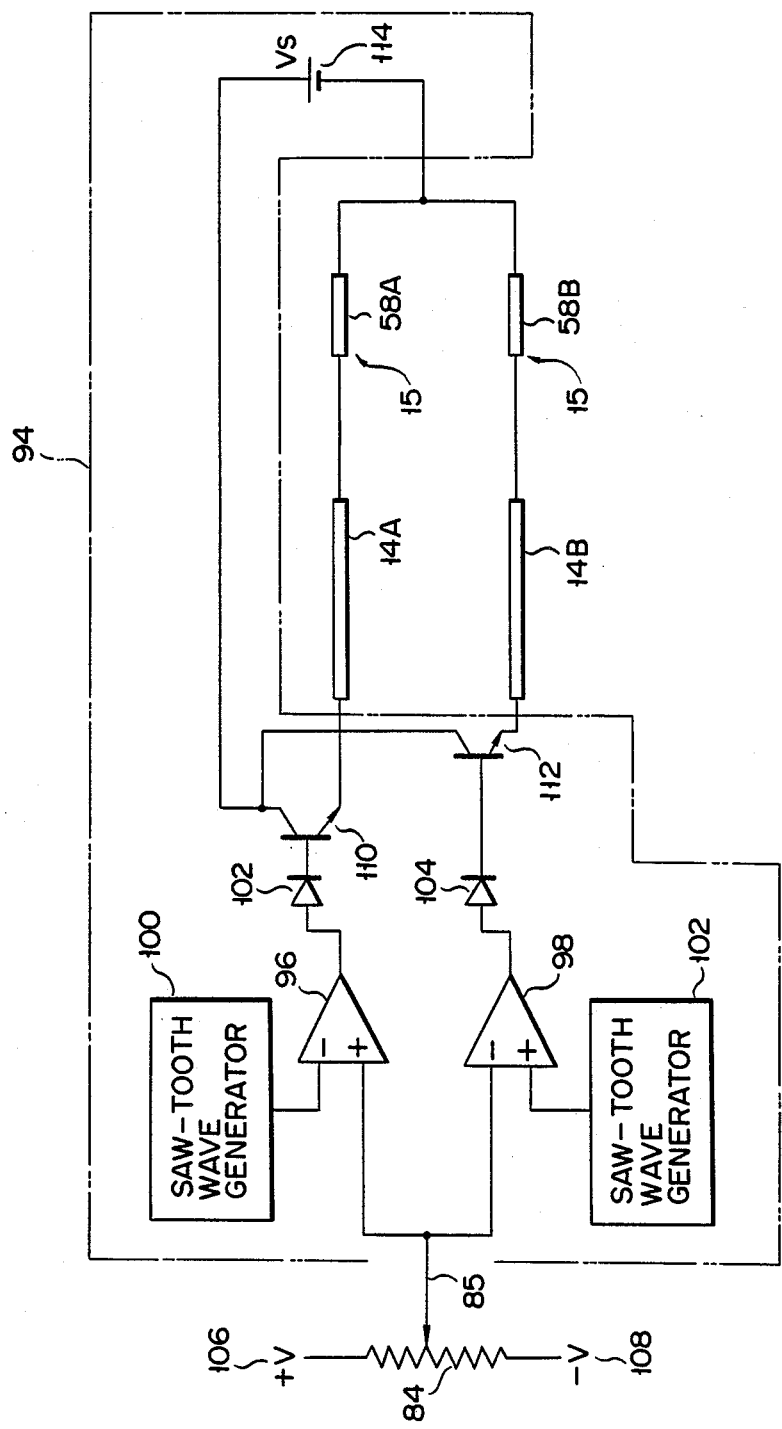
F I G. 12

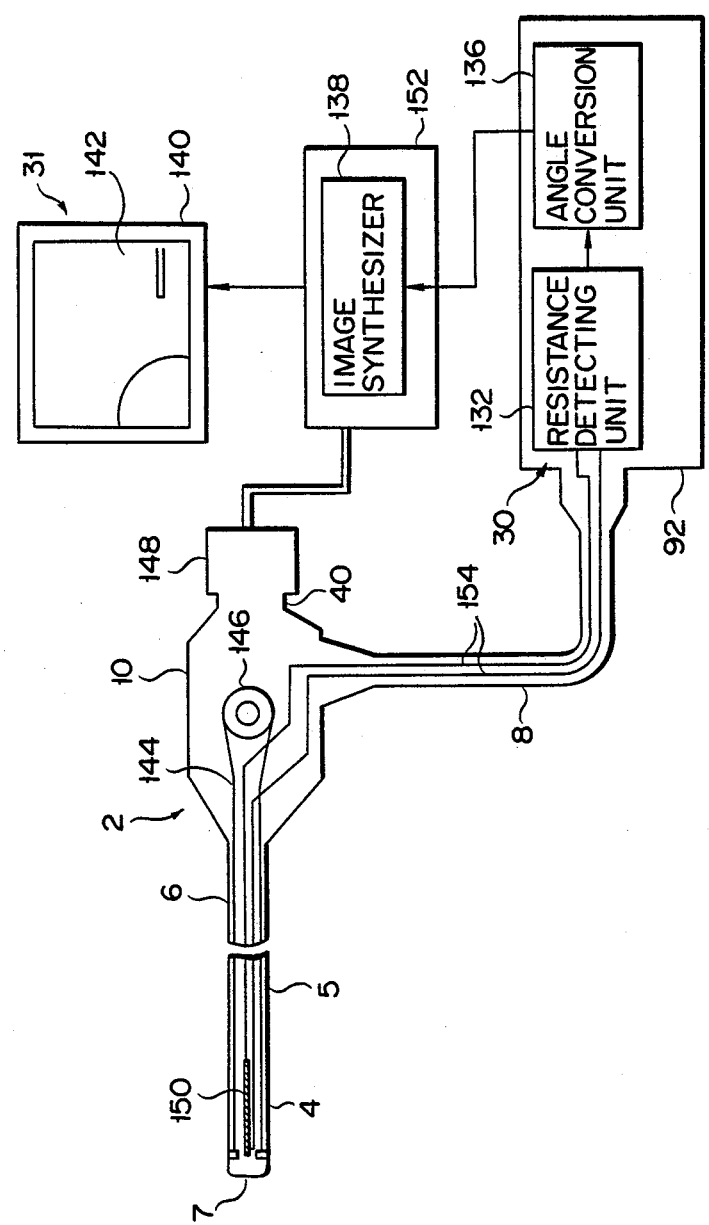
F I G. 20

ENDOSCOPE

This application is a continuation of application Ser. No. 106,248, filed Oct. 7, 1987, now abandoned.

BACKGROUND OF THE INVENTION

1. Field of the Invention

The present invention relates to an endoscope for use in observation of internal tissue of a living body under examination or an endoscope for industrial use and, more particularly, to an endoscope which has a device that displays the bending state of a bending section provided at the distal end of its insertion section.

2. Description of the Prior Art

A typical endoscope has an insertion section and an operating section and permits a bending section provided at the distal end of the insertion section to be bent in the desired direction through manual operation of a bending manipulation wire that is disposed within the insertion section.

Recently, in place of the above manual-operation type endoscope, different type of endoscopes have been developed which have a motor assembled within the operating section as a driving device to operate the bending manipulation wire in the insertion section, or which have a shape memorizable alloy disposed within the insertion section and permit the bending section to be bent by heating the shape memorizable alloy.

With the mechanical driving type of endoscopes, unlike the manual operation type, an operator cannot feel, through his or her hands, how much the bending section has been bent.

To cope with this problem, therefore, as disclosed in Japanese Utility Model Disclosure No. 60-106601 and Japanese Patent Disclosure No. 61-79439, for example, a device has been proposed which detects a bent angle of the bending section from the length of the bending manipulation wire moved.

However, if the endoscope's insertion section, when inserted into a body, bends along the body interior wall, the length of the bending manipulation wire moved does not coincide with the moved length of the wire in the case where the insertion section is inserted without bending. In this case, therefore, it is difficult for the above-mentioned bent-angle detecting device to accurately detect the bent angle of the bending section. For instance, even with the moved length of the bending manipulation wire being the same for both cases, if portion of the insertion section is bent, the bent angle of the bending section would change. Specifically, the wire that bends with bending of the insertion section absorbs the tension at the operating section and stretches due to the tensile strength caused by the bending of the insertion section. As a result, it is difficult to accurately detect the bent angle of the bending section.

SUMMARY OF THE INVENTION

With the above circumstances in mind, it is an object of this invention to provide an endoscope capable of accurately detecting the bent angle of its insertion section.

This object is achieved by providing an endoscope with an operating section and insertion section having a bending section, which has the following structure. A bending member formed of a shape memorizable alloy is disposed within the bending section of the insertion section to bend the bending section, and a power supply unit is connected to this bending member. The endoscope further comprises detecting means for detecting an amount of deformation of the bending member, and display means for displaying the amount of deformation of the bending member.

With the above structure, the endoscope of this invention can accurately detect the bending amount or the bent angle of the bending section of the insertion section and display it for easier confirmation by an operator so that the operator can safely manipulate the endoscope.

BRIEF DESCRIPTION OF THE DRAWINGS

FIG. 1 is a schematic diagram illustrating an endoscope according to the first embodiment of this invention;

FIG. 2 is a side view of a bending member of the first embodiment;

FIG. 3 is a transverse cross-section of a bending member taken along line A—A of FIG. 2;

FIG. 10 is a vertical cross-section of a bending display section shown in FIG. 9;

FIG. 11 is a schematic diagram of a modification of the endoscope according to the second embodiment;

FIG. 12 is a circuit diagram illustrating an operating circuit for the bending section and display section shown in FIG. 11;

FIG. 20 is a schematic diagram showing a modification of the endoscope according to the third embodiment.

DETAILED DESCRIPTION OF THE PREFERRED EMBODIMENTS

Figure 4:
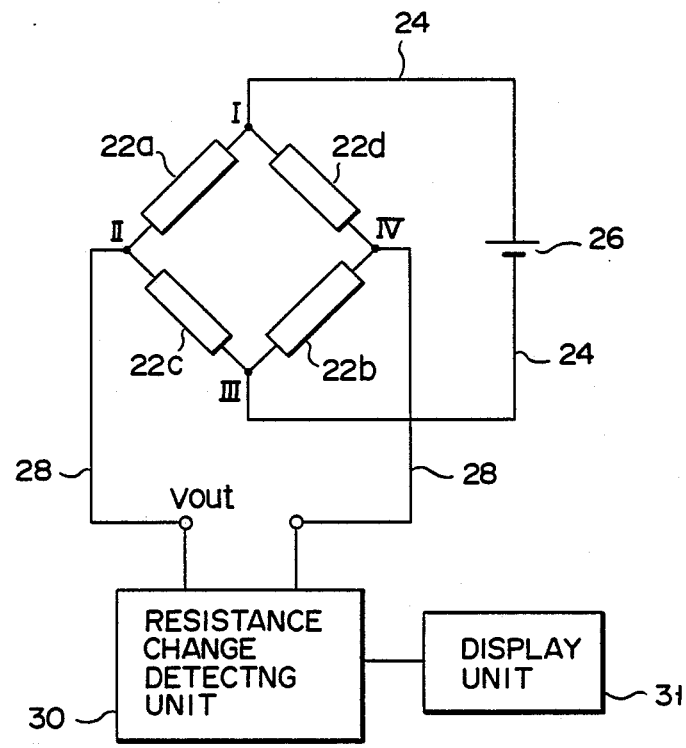
FIG. 4 is a circuit diagram of a bent angle detector for use in the first embodiment.

Embodiments of this invention will be explained below referring to the accompanying drawings.

FIGS. 1 through 6 illustrate an endoscope according to the first embodiment of this invention. An endoscope 2 schematically shown in FIG. 1 has an operating section 10 and an insertion section 6. A bending section 4, which is manipulated through operating section 10, is provided at the distal end of insertion section 6. A universal cord 8, which couples operating section 10 and a power supply unit 20, is connected to operating section 10. A bending mechanism 12 provided with a shape memorizable alloy is disposed within bending section 4. More specifically as shown in FIGS. 2 and 3, bending mechanism 12 has a belt-shaped driving bending member 14 that is formed of a shape memorizable alloy (SMA), such as a Ti-Ni alloy or Cu-Zn-Al based alloys. This bending member 14 is disposed in bending section 4 long the axial direction thereof. According to the first embodiment, bending member 14 has a deformation temperature set to about 60° C. and a shape memorized so that the bending member 14, after deformation, would take the form as indicated in FIG. 2. A pair of power supply cables 16 are connected at one end to the respective ends of bending member 14. The other end of one of the cables 16 extends through insertion section 6, is connected to a switch 18 provided in operating section 10, and extends through universal cord 8 to the outside to be connected to power supply unit 20. The other end of the remaining cable 16 extends through insertion section 6 and universal cord 8 to the outside and is also connected to power supply unit 20. Through manipulation of switch 18, therefore, bending member 14 can be supplied with power to be heated so as to bend bending section 4.

As illustrated in FIG. 3, the surface of bending member 14 formed of a shape memorizable alloy is adhered with four belt-shaped conductive rubbers 22a to 22d, or detecting means 13, so that the amount of bending of bending member 14 can be detected from a change in electric resistance of these conductive rubbers 22a-22d.

Specifically, conductive rubbers 22a-22d may be formed by dispersing conductive particles or metal fillers in a rubber material. The first embodiment employs conductive rubbers 22a-22d that are formed by uniformly dispersing carbon particles in a silicone rubber. As illustrated in FIGS. 2 and 3, conductive rubbers 22a-22d are adhered two on each surface of bending member 14 in a symmetrical fashion such that conductive rubbers 22a and 22b respectively face the remaining rubbers 22c and 22d with bending member 14 in between. As illustrated in FIG. 4, conductive rubbers 22a-22d are connected to a bridge circuit, and a node I between conductive rubbers 22a and 22d and a node III between conductive rubbers 22b and 22c are connected to one ends of electric cables 24 inserted in inserting section 6. The cables 24 are further connected at the other end to a power supply 26. Accordingly, nodes I and III are applied with a given voltage. A node II between conductive rubbers 22a and 22c and a node IV between conductive rubbers 22b and 22d are connected to one ends of electric cables 28 also inserted in inserting section 6. The cables 28 are further connected at the other end, for example, to a resistance change detecting unit 30, that is detecting means, provided in operating section 10. By detecting a change in voltage at nodes II and IV which corresponds to a change in resistance of conductive rubbers 22a-22d, therefore, the amount of deformation of bending unit 4 can be indirectly detected. Resistance change detecting unit 30 is connected, for example, to a display unit 31 that indicates the amount of deformation of bending section 4.

Bending section of endoscope 2 is gradually bent by heating bending member 14 made of a shape memorizable alloy, and the resistances of conductive rubbers 22a-22d vary with a change in bent angle $\theta$ (see FIG. 2) or in the amount of deformation. In this case, the stretching amount of conductive rubbers 22a-22d as well as their resistances are proportional to bent angle $\theta$.

The relationship between bent angle $\theta$ of bending section 4 and the contracting amount of conductive rubbers 22a-22d will now be explained. This explanation will be given on the following premise. Bending member 14 has a thickness c, conductive rubbers 22a-22d disposed on both sides of the member 14 has a thickness b and a length l, and the angle defined by both ends of the conductive rubbers is $\theta$.

Figure 6:
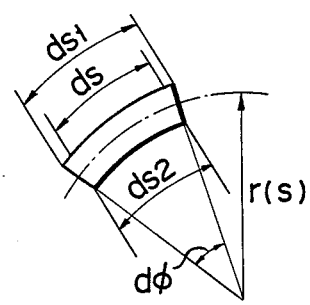
FIG. 6 is a segmentary view illustrating a bending state of a bending member.

Let us now consider a line portion ds on the center line of the bending member within a small portion encircled by a two-dot chain line X in FIG. 2. Suppose that, as shown in FIG. 6, the deformation within a small length ds is a circular arc with a radius of curvature at a point separated by a length s from one end $\alpha$ of a conductive rubber being r(s). Then, the strains $\epsilon_1$ and $\epsilon_2$ of upper and lower surfaces of a to-be measured section is expressed as follows:

$$\epsilon_1 = \frac{ds_1 - ds}{ds} = \frac{b+c}{2r(s)}$$

$$\epsilon_2 = \frac{ds_2 - ds}{ds} = -\frac{b+c}{2r(s)}$$

And, the amounts of overall stretch $\Delta l_1$ and $\Delta l_2$ are $$\Delta l_1 = \int_0^1 \epsilon_1 ds = \int_0^\theta \frac{b+c}{2r(s)} r(s)d\phi = \frac{b+c}{2}\theta$$

$$\Delta l_2 = -\frac{b+c}{2}\theta$$

From the above, therefore, it is understood that irrespective of the deformed shape between $\alpha$ and $\beta$, the amounts of contraction of conductive rubbers 22a-22d are proportional to the angle $\theta$ defined by both ends of the rubbers.

Figure 5:
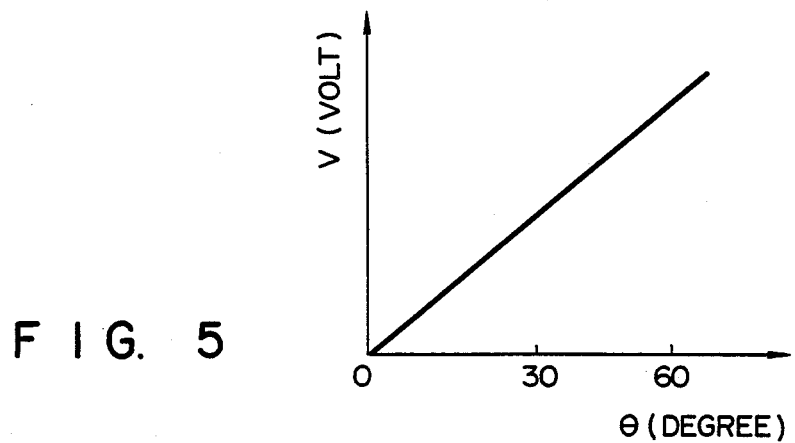
FIG. 5 is a graph showing the relationship between a bent angle of a bending member and an output voltage V.

In other words, given the relationship between the electric resistance and stretching amounts of conductive rubbers 22a-22d, the bent angle $\theta$ can be accurately be derived. Experiments conducted yielded the proportional relationship between the bent angle $\theta$ and the voltage between nodes II and IV as shown in FIG. 5. And from the relationship the bent angle $\theta$ can be attained by detecting the voltage between nodes II and IV.

Figure 7:
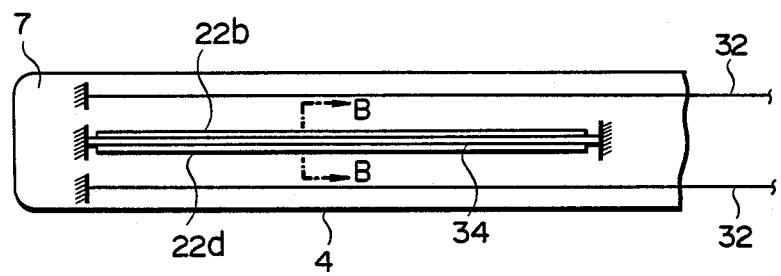
FIG. 7 is a schematic diagram of a modification of the endoscope according to the first embodiment.
Figure 8:
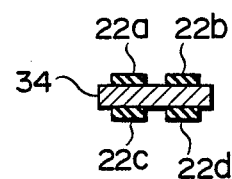
FIG. 8 is a vertical cross-section of a bending member taken along line B—B of FIG. 7.

FIGS. 7 and 8 illustrate the first modification of the endoscope according to the first embodiment. In the modification, a deformation-amount detector is assembled in the endoscope in which the distal end of a ending manipulation wire 32 is fixed to a distal end member 7 of insertion section 6, and bending portion 4 is bent by mechanically manipulating bending manipulation wire 32. In bending section 4 is disposed a resilient member 34, such as a rubber plate, in place of a shape memorizable alloy, and conductive rubbers 22a-22d are adhered to the respective surfaces of rubber plate 34, as is the case in the first embodiment. Therefore, the bending amount of the bending section can be detected as per the first embodiment.

This invention is not limited to the above embodiment or modification. The conductive rubbers may be provided anywhere in the insertion section as long as their mounting location is to be subjected to detection of the bending amount. For instance, conductive rubbers may be provided in a bendable tube portion in the insertion section other than the bending section to detect the amount of deformation of the bendable tube portion or may be provided at a plurality of portions in the axial direction in the insertion section to detect a change in shape of each portion. Further, conductive rubbers may be provided on the inner wall of the insertion section along the circumferential direction or may be embedded under the bending rubber that forms the outer cover of the insertion section.

The insertion section of the endoscope according to the first embodiment bends in one direction while the insertion section of the modification bends in two direction. However, a plurality of bending members made of a shape memorizable alloy may be provided according to the number of the bending members in order to detect the bending amounts in many directions.

The detected bent angle or bending amount can be displayed within a field of view of a viewing section of the endoscope or can be displayed on a TV monitor.

Based on the detected bent angle or bending amount, for example, a voltage applied to the bending member may be adjusted so that the bending section can be bent to the desired angle or kept at a given angle.

In addition, the bent angle may be attained by detecting a change in resistance due to the phase transformation of the compounds of a shape memorizable alloy (e.g., lower temperature side: martensite phase, and higher temperature side: austenite phase) that depends on a change in temperature.

Figure 9:
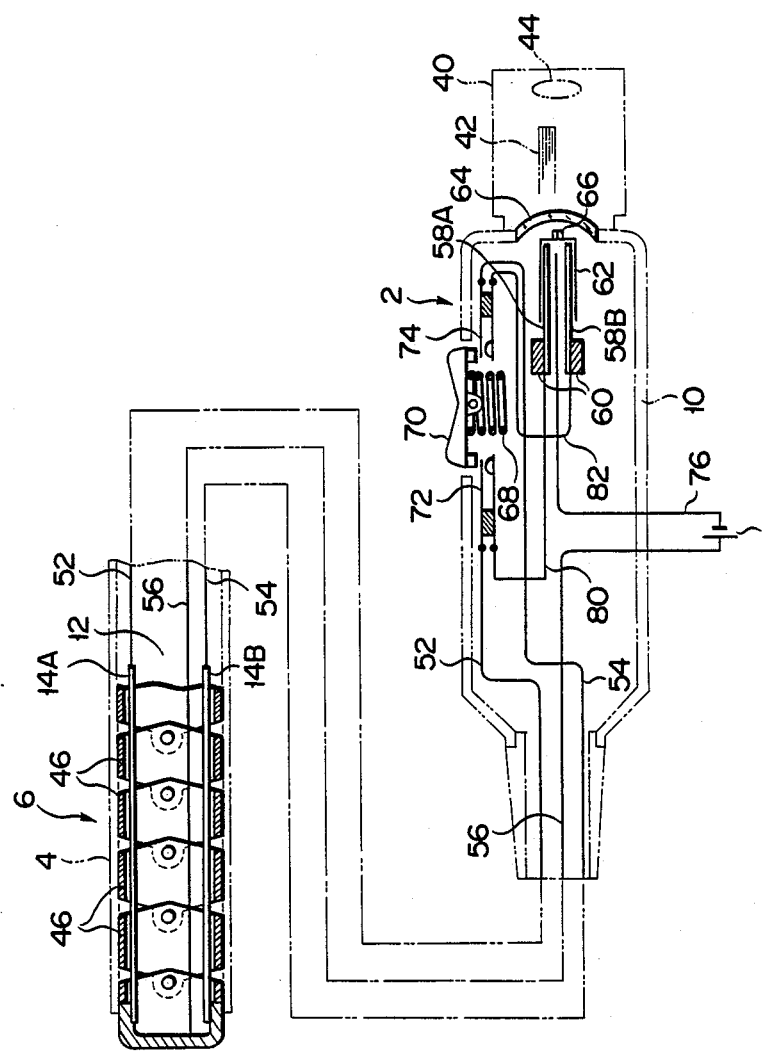
FIG. 9 is a schematic diagram illustrating an endoscope according to the second embodiment of this invention.

Referring now to FIGS. 9 and 10, the second embodiment of this invention will be explained. An endoscope 2 schematically shown in FIG. 9 comprises an operating section 10, an insertion section 6 and a universal cord (not shown) having a built-in light guide. An image guide 42 is disposed within insertion section 6 and operating section 10, with its one end of the image guide being coupled to the distal end of insertion section 6 and the other end coupled to a viewing section 40 of operating section 10. An observational optical system is constituted by the image guide 42 and an optical lens 44 disposed facing the base portion of image guide 42.

At the distal end portion of insertion section 6 is provided a bending section 4 that is constituted by a plurality of bending segments 46. A bending mechanism 12 to bend the bending section 4 is provided with a pair of driving bending members 14A and 14B made of a shape memorizable alloy. Accordingly, bending section 4 can be bent by deformation of the shape memorizable alloy. The belt-shaped bending members made of, for example, a Ti-Ni alloy or a cu-Zn-Al-based alloy are disposed inside bending segments 46 in the axial direction, and each bending member remembers its bending shape at a deformation temperature. Bending members 14A and 14B are connected at the proximal end to lead wires 52 and 54, respectively, and are also connected at the distal end to a lead wire 56. The individual bending members 14A and 14B can be heated up to be bent by supplying current to these members 14A and 14B through the lead wires.

According to the second embodiment, a pair of display bending members 58A and 58B, or display means 15, made of a shape memorizable alloy are provided in operating section 10 in a visible manner. Bending members 58A and 58B are short plate members formed, for example, of a ti-Ni alloy or a Cu-Zn-Al based alloy. These bending members 58A and 58B are supported to be parallel to each other and a bendable tube 62 is fit over the exposed portions of the members 58A and 58B. Therefore, bendable tube 62 moves the same way as bending section 4.

An opening of a belt-shape, for example, is formed in the wall of the rear portion or operating section 10 that is adjacent to viewing section 40, and is attached with a transparent arc-shaped cover 64. Display bending members 58A and 58B together with tube 62 are disposed inside cover 64 in the axial direction in operation section 10, and an indicator 66 is mounted at the bottom of tube 62 so that the indicator can be viewed through cover 64 from the outside.

The bending amount of bending section 4 can be indicated by simultaneously supplying current to driving bending members 14A and 14B of bending section 4 and display bending members 58A and 58B.

At the side wall of operating section 1 is mounted a seesaw type operation button 70 that is horizontally supported by a spring 68. Contacts 72 and 74 are provided below both of the bottom ends of operation button 70. The proximal end of lead wire 52 that is connected to bending member 14A of bending section 4 is connected in series to bending member 58A through contact 74. Lead wire 56 and another lead wire 76 that is connected to end portions of bending members 58A and 58B are connected to a power supply 78 disposed outside the operating section 10. A lead wire 80 connects contact 72 and bending member 58A while a lead wire 82 connects contact 74 and bending member 58B. Consequently, depressing one end of operation button 70 bends bending members 14A and 58A upward, while depressing the other end of operation button 70 bends bending members 14B and 58B downward.

According to the endoscope of the second embodiment, depressing one end of operation button 70 closes contact 72 to simultaneously supply power to both of bending member 14A of bending section 4 and the second bending member 58A of operating section 10. As a result, bending members 14A and 58A are heated and gradually bent upward. Consequently, it is possible to display a bending amount that is proportion to the bending of the distal end of bending section 4.

As an operator can see indicator 66 through transparent cover 64 and confirm the bending amount of bending section 4, the operator can safely manipulates the endoscope. Further, driving bending members 14A and 14B are coupled in series to display bending members 58A and 58B, respectively, so that when disconnection occurs in the circuit, the bending members do not bend and the damaged portion can easily be found. Indicator 66 may be provided within the field of view of viewing section 40 so that the operator can confirm the present bending amount without taking his or her eyes off viewing section 40.

Referring now to FIGS. 1 through 14, a modification of the endoscope according to the second embodiment will be explained. In this modification, a potentiometer 84 is used to bend the bending section 4 and display bending members 58A and 58B to a given angle.

More specifically, coil springs 86 and 88 that have substantially the same elasticity are disposed in bending section 4 and bendable tube 62, and driving bending members 14A and 14B are coupled in series to display bending members 58A and 58B, respectively. An operating lever 90 is mounted to an axial portion 84A of potentiometer 84 in operating section 10. Potentiometer 10, series-coupled bending member 14A and 58A and other series-coupled bending member 14B and 58B are connected to a bending controller 94 that is provided in a light source device 92.

Bending controller 94 comprises two comparators 96 and 98 as shown in FIG. 12. A non-inverting input terminal of the first comparator 96 and inverting input terminal of the second comparator 98 are coupled to a center terminal 85 of potentiometer 84 to which positive and negative power supplies 106 and 108 are coupled. An inverting input terminal of first comparator 96 and a non-inverting input terminal of second comparator 98 are respectively coupled to saw-tooth wave generator 100 and 102 which generate a saw-tooth wave as shown at the upper part of FIG. 13. The outputs of comparators 96 and 98 are respectively coupled to diodes 102 and 104. When operating lever 90 linked to center terminal 85 is rocked in one direction, therefore, a positive voltage (+V) having the necessary potential is intermittently output from the first diode 102. When operating lever 90 is rocked in the opposite direction, a positive voltage (+V) is output from the second diode 104. These diodes 102 and 104 are respectively coupled to the bases of transistors 110 and 112. The first transistor 110 has its emitter coupled to bending member 14A, while the second transistor 112 has its emitter coupled to bending member 14B. The collectors of transistors 110 and 112 and display bending members 58A and 58B ar coupled to a power supply (Vs) 114. Therefore, adjusting the amount of the power supplied to the individual bending members 14A, 14B, 58A and 58B deforms these bending members and the bending amount of bending section 4 is kept constant at the balancing point between the deforming strength and the elasticity of the individual coil springs 86 and 88.

Bending controller 94 is coupled to endoscope 2 through a universal cord 8B that has at its distal end a connector 8A detachably coupled to a socket (not shown) of light source device 92. Components necessary for endoscopic observation such as a light sourcer, a assembled in light source device 92.

The following is an explanation of the operation of endoscope 2 according to this modification. For instance, when operating lever 90 is rocked in one direction, center terminal 85 of potentiometer 84 moves toward power supply 106. When the non-inverting input terminal of first comparator 96 is applied with a voltage of $+V_1$, comparator 96 generates a pulse voltage as indicated by the solid line at the lower part of FIG. 13. The pulse voltage triggers firs transistor 110 to supply power to bending members 14A and 58A.

Consequently, forces for bending the bending members 14A and 58A upward are generated in these members, and the bending stops at the position where the generated forces are balanced with elasticity of coil springs 86 and 88, thus ensuring that a constant amount of bending can be maintained. At the same time, the bending amount of bending section 4 is displayed on the display section.

Figure 13:
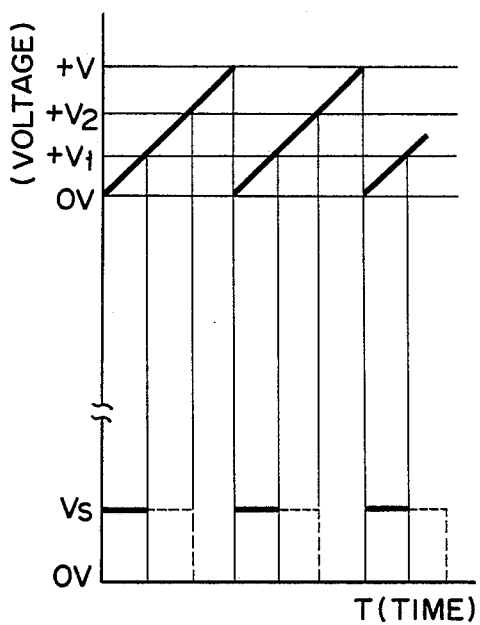
FIGS. 13 and 14 are graphs illustrating drive pulses for the bending member.
Figure 14:
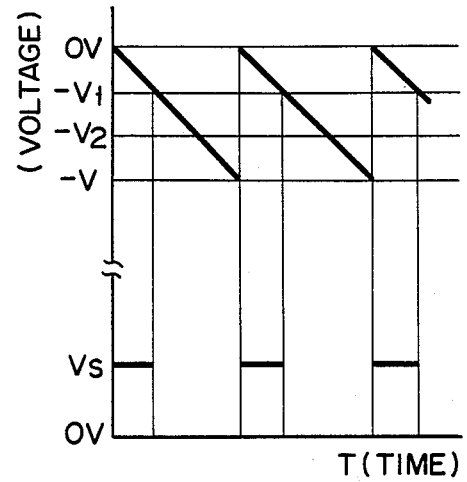

When operating lever 90 is further rocked in the same direction to apply a $+V_2$ voltage to center terminal 85 of potentiometer 84, first comparator 96 produces a pulse voltage indicated by the broken line at the lower part of FIG. 13 and the amount of power supplied to bending members 14A and 58A is increased accordingly. And, bending members 14A and 58A bend further upward from the previous position and the bending stops at a position where the generated bending force is balanced with the elasticity of coil springs 86 and 88. When center terminal 85 of potentiometer 84 is moved toward power supply 106, bending members 14B and 58B are not energized.

When operating lever 90 is rocked in the opposite direction, center terminal 85 of potentiometer 84 is applied with a negative voltage and bending members 14B and 58B are bent in the other direction. For instance, when the center terminal of potentiometer 84 is applied with a $-V_1$ voltage, second comparator 98 produces a pulse voltage as indicated at the lower part of FIG. 14 to trigger transistor 112. As a result, bending members 14B and 58B are energized so that these members 14B and 58B are bent in the other direction and the bending stops at a position where the bending force is balanced with the elasticity of coil springs 86 and 88.

Figure 15:
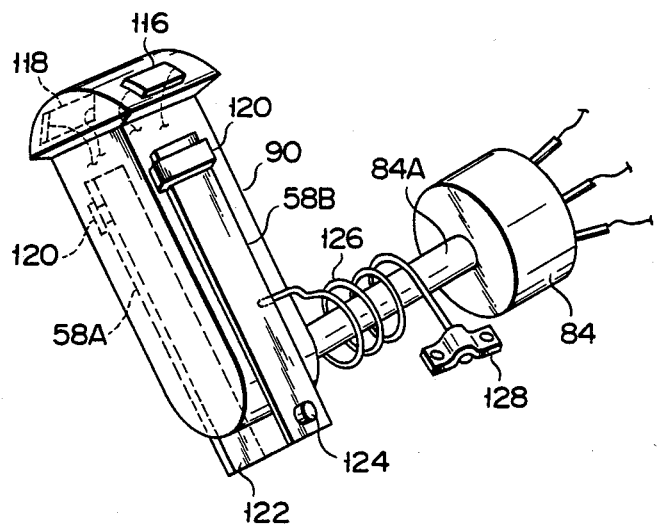
FIG. 15 is a perspective view illustrating a modification of the bending display section for use in the second embodiment.
Figures 16, 17:
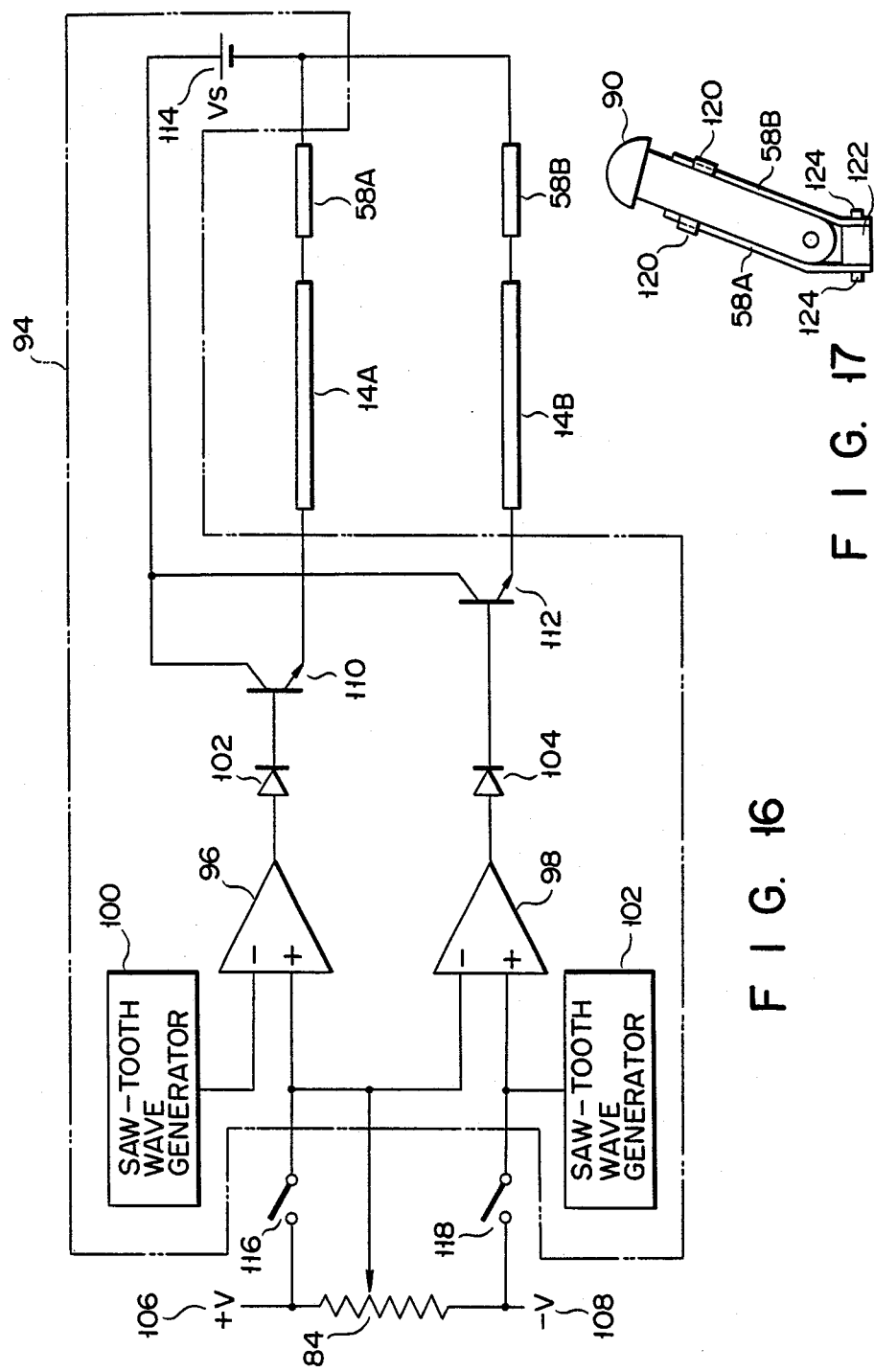
FIG. 16 is a circuit diagram illustrating an operating circuit for a display section for use in the modification shown in FIG. 15.
FIG. 17 is a side view of an operating lever for use in the same modification.

Referring now to FIGS. 15 to 17, a modification of the bending display section will be explained below. In this modification, display bending members 58A and 58B formed of a shape memorizable alloy and switches 116 and 118 used for bending operation are mounted to operating lever 90 so that the operator can confirm the bent angle of bending section 4 visually and through hands.

The switches 116 and 118, which may be formed of piezo-electric rubbers, are respectively mounted on the front and back of the head portion of operating lever 90. As illustrated in FIG. 16, first switch is inserted between power source 106 applied with a voltage (+V) of potentiometer 84 and the non-inverting input terminal of first comparator 96. Therefore, turning on first switch 116 supplies a +V voltage to comparator 96. Second switch 118, which is inserted between power source 108 applied with a voltage (-V) of potentiometer 84 and the non-inverting input terminal of second comparator 98. Therefore, turning on second switch 118 supplies a -V voltage to second comparator 96.

As illustrated in FIG. 15, display bending members 58A and 58B that are formed of a shape memorizable alloy are respectively adhered to the front and back surfaces of operating lever 90. Bending members 58A and 58B disposed in parallel to each other are fixed at one end to the side surfaces of operating lever 90 by fixing members 120. Those of bending members 58A and 58B protruding from the bottom portion of operating lever 90, are fixed to a fixing section 122 provided in operating section, by means of a pin 124. Therefore, depressing either first switch 116 or second switch 118 bends bending member 58A and 58B in the direction of the switch depressed and rotates the overall operating lever 90. A coil spring 126 is disposed around a shaft portion 84A of potentiometer 84, and has one end fixed to operating lever 90 and the other end fixed to the housing of operating section 10 by means of a metal fitting 128. Coil spring 126 has an elasticity that is balanced with the force generated when operating lever 90 is bent maximum, i.e., the deforming force of shape memorizable alloys 58A and 58B. In this modification, therefore, the maximum value of the rocking angle of operating lever 90 is limited.

Since the amount of power that should be supplied to bending members 58A and 58B is set by the rotational angle of potentiometer 84, the rotation angle of operating lever 90 is held at the position corresponding to the bent angle of bending section 4. Bending section 4 is provided with coil spring 86 which has an elasticity that matches the bending force at the time driving bending members 14A and 14B bend maximum.

The operation of the endoscope to which this modification is directed will now be explained. When first switch 116 of endoscope 2 is depressed, the contact is turned ON and a voltage +V is supplied to first comparator 96. Consequently, the output of comparator 96 becomes a continuous signal Vs and bending member 14A of bending section 48 and bending member 58A of operating lever 90 are energized and gradually bend. When bending members 84 bends to the maximum level, the bending force matches with the elasticity of coil spring 86 and the bending state is maintained. At the same time, as illustrated in FIG. 17, operating lever 90 is rocked in the direction of switch 116 by display bending member 58A. When operating lever 90 bends maximum, however, the bending force matches with the elasticity of coil spring 126 and the bending stops at that position.

During depression of first switch 116, therefore, operating lever 90 gradually bends in the direction depressed, so that the operator can feel how the position of operating lever 90 is changed through the operator's hands. That is, this endoscope provides an accurate confirmation of a bending amount through hands as well as eyes.

When the first switch 116 is released at the desired position while the bending amount of operating lever 90 is being detected by the feeling of hands, a pulse voltage sent in advance by potentiometer 84 is output from comparator 96. And, this pulse voltage energizes bending members 14A and 58A and operating lever 90 and bending section 4 are held at the bending position attained upon release of switch 116.

In the aforementioned second embodiment and its modification, a bending display mechanism is assembled in an endoscope that bends in the up and down or right and left direction. However, the bending display mechanism may be incorporated into an endoscope which can bend in any direction, up and down and right and left.

Referring now to FIGS. 18 through 22, the third embodiment of this invention will now be explained.

Figure 18:
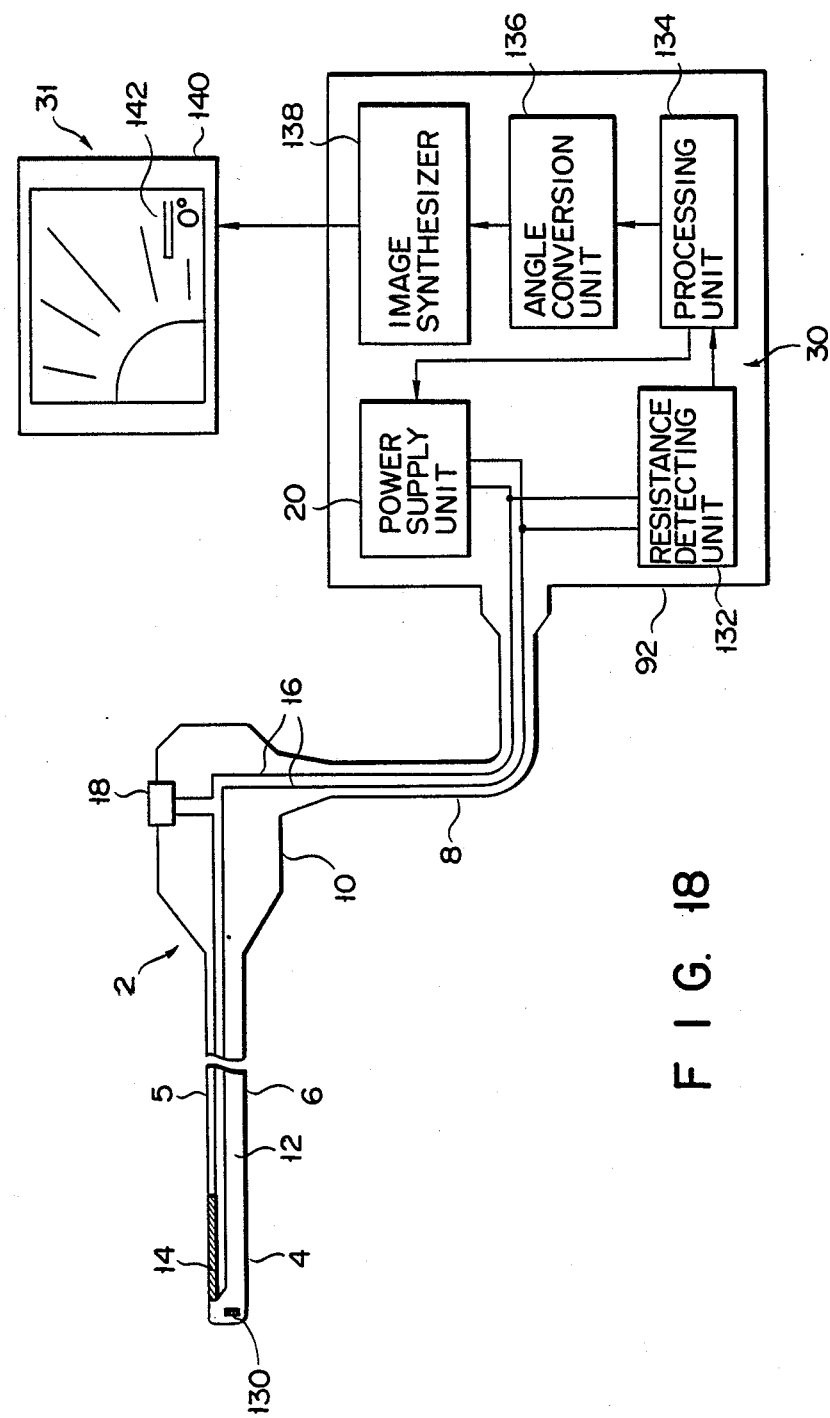
FIG. 18 is a schematic diagram illustrating an endoscope according to the third embodiment of this invention.
Figure 19:
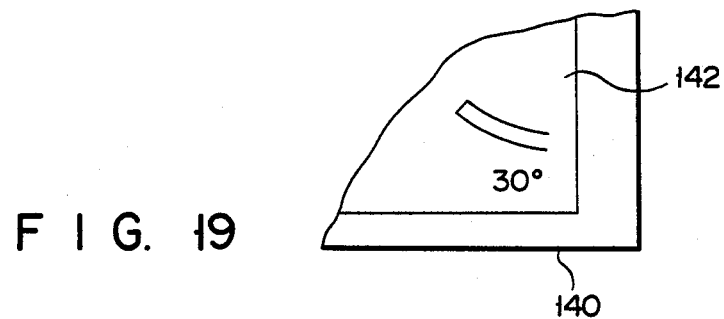
FIG. 19 is a segmentary view illustrating a display section of a TV monitor shown in FIG. 18.

FIG. 18 illustrates an industrial endoscope 2 for use in checking inside a tube interior, for example. An endoscope or an electronic scope 2 comprises an operating section 10 and an insertion section 6, which comprises a bendable tube 5, a bending section 4 linked to the distal end of bendable tube 5 and a distal end constituting section 7. A universal cord 8 having a light guide (not shown) assembled therein is coupled to operating section 10. A solid state image pickup device 130 for converting an optical image into a TV signal are assembled at the distal end of insertion section 6. Within bending section 4 is disposed a bending mechanism 12 that has bending member 14.

In bending mechanism 12, bending member 14 formed in belt shape of a shape memorizable alloy (SMA) such as a Ti-Ni alloy or a Cu-Zn-Al-based alloy is provided within bending section 4 in the axial direction, and this bending member 14 remembers the necessary bending state that has been set in advance. Both ends of bending member 14 is connected to a power supply unit 20 assembled in light source device 92 of endoscope 2, by means of a power cable 16 that extends through universal cord 8 and insertion section 6. Operating section 10 is mounted with a switch 18 for power supply control. Therefore, by manipulating the operating switch 18, bending member 14 is heated up to be bent.

In addition to power supply unit 20, a resistance detecting section 132 to be electrically coupled to cable 16, a processing unit 134, an angle conversion unit 136 and image synthesizer 138 are assembled in light source device 92. Power supply unit is coupled to processing unit 134 so that bending member 14 can be heated using a pulse of a PWM (Pulse Width Modulation) system. Controller 134 is also coupled to resistance detecting unit 132 so as to cause resistance detecting unit 132 to detect a change in electric resistance in the bending member or shape memorizable alloy 14 using a time during which a pulse energization is stopped.

It should be noted that the electric resistance of a shape memorizable alloy varies with phase transformation from a martensite phase or rhonbohedral phase of a lower temperature to an austenite phase of a higher temperature. The same can apply to the opposite phase transformation.

Processing unit 134 is connected to angle conversion unit 136 to calculate the present bent angle from the electric resistance corresponding to the bending amount of the shape memorizable alloy. Angle conversion unit 136 is connected to image synthesizer 138 which is coupled to a TV monitor 140 that displays in an image form the TV signal from solid state image pickup device 130. As a result, the bending amount of bending section 4 can be synthesized with an observed image and the resultant image can be displayed on the TV screen.

In the third embodiment, the lower right corner of TV monitor 140 is utilized as bending display section 142 on which the present bent angle $\theta$ of bending section 4 is numerically displayed and at the same time the shape of ending section 4 is displayed as a pseudo image.

To maintain the necessary bent angle $\theta$ for bending section 4, power supply unit 20 receives a control signal from processing unit 134 so as to adjust the conductive amount of bending member 14. Therefore, it is possible to maintain a bent angle, for example, of 30°.

The operation of the industrial endoscope according to the third embodiment will now be explained.

First, light source device 92 and TV monitor 140 are coupled to endoscope 2. Then, inserting section 6 is inserted into a tube (not shown) to be subjected to checking. As a result, an optical image picked up by solid image pickup device 130 is displayed on the screen of TV monitor 140 through a video processor (not shown). The bending state is displayed on bending display section 142 of TV monitor 140.

More specifically, the phase of shape memorizable alloy 4 at the time the insertion section is fit in the tube is a martensite phase of a lower temperature, and non-deformation of the shape memorizable alloy is determined by detecting the electric resistance of the martensite phase by resistance detecting unit 132. The electric resistance corresponding to the amount of deformation of shape memorizable alloy 14 is calculated in angle conversion unit 136 to provide a bent angle of 0°. Then, as illustrated in FIG. 18, image synthesizer 138 synthesizes the numeral "0" and a pseudo image indicating that bending section 4 is straight with an observed image and then displays the resultant image on TV monitor 140.

When switch 18 is operated, a pulse current is supplied to shape memorizable alloy 14 from power supply unit 20. This pulse current heats up shape memorizable alloy 14 so that the alloy is gradually transformed into an austenite phase. In other words, shape memorizable alloy 14 is transformed to have a pre-memorized bending state or a circular arc shape so that ending section 4 gradually bends in an arc shape. At the same time, the bending amount of bending section 4 is displayed on bending display section 142 of TV monitor 140 in the form of the bent angle and a pseudo image corresponding to the above-mentioned bent angle.

When power supply unit 20 is in operation, resistance detecting unit 132 detects the electric resistance at the time shape memorizable alloy 14 is transformed into the austenite phase, by utilizing the time when pulse current is stopped. The resistance is converted into an angle by angle conversion unit 136, and the bending state is displayed in numeral and diagram by image synthesizer 138. For instance, when bending section 4 bends at angle of 30° through power control, bending display section 142 displays "30°" and a pseudo image corresponding to the bent angle above the numeral, s illustrated in FIG. 19.

Therefore, the operator can accurately confirm the amount of deformation of insertion section 6 by viewing display section 142 and can thus safely manipulate endoscope 2.

In the third embodiment, a bending display mechanism is assembled in an endoscope with a bending section in which bending members made of a shape memorizable alloy are disposed. This invention can also apply to a fiber scope, a typical endoscope, which has an angle wire 144 and a drum 146 as illustrated in FIGS. 20 and 21, is subjected to a manual bending operation, and transfers an image to a viewing section 40 through a fiber.

According to a modification of the endoscope of the third embodiment, a camera head 148 is attached to viewing section 40 of an endoscope 2 and an observed image is displayed on a TV monitor 140. Inside a bending section 4 there is a belt-shaped conductive rubber or bending amount detecting section 150 so that a bending amount can be detected by a change in electric resistance that is caused by stretching of conductive rubber 150.

More specifically, camera head 148 is coupled to TV monitor 140 through a camera controller 152. An optical image from endoscope 2 that is converted into an electric signal by camera head 148 is converted into a TV signal by camera controller 152 and is displayed on TV monitor 140. Conductive rubber 150 is coupled at both ends to a resistance detecting section 132 incorporated in a light source device 92, through signal lines 154, and the resistance detecting section 132 is coupled to an image synthesizer 138 of camera controller 152 through an angle conversion circuit 136 assembled in light source device 92. Resistance detecting section 132 detects a change in electric resistance of conductive rubber 150 that stretches with bending of bending section 4. Angle conversion circuit 136 calculates a bent angle from the detected electric resistance. As is the case in the third embodiment, image synthesizer 138 displays on TV monitor 140 an endoscopic image together with the bending state that is represented by a numeral indicating the bent angle and a pseudo image.

Figure 21:
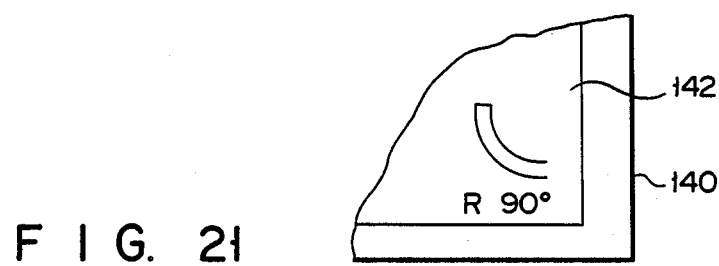
FIGS. 21 and 22 are segmentary views illustrating a display section of a TV monitor shown in FIG. 20.

Further, in this modification, it is possible to detect the rotational direction of drum 146 and display it by a numeral "R" (right) or "L" (left) besides the numeral indicating the bent angle, as shown in FIG. 21. This bent angle displaying mechanism can apply to an endoscope in which angle wire 144 is driven by a motor.

Figure 22:
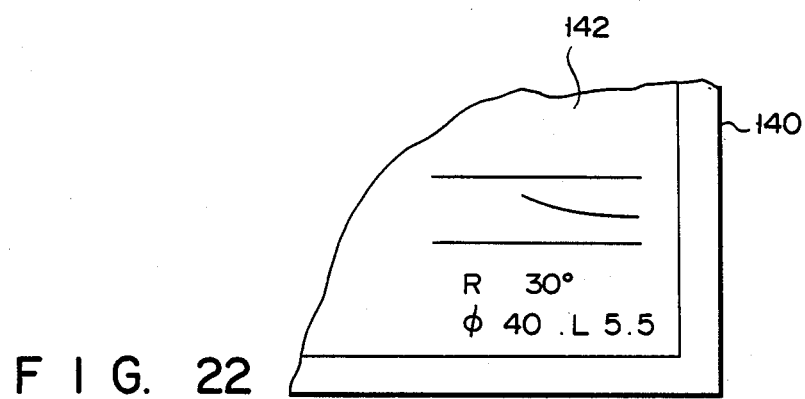

In the above third embodiment and its modification, the bending direction, bent angle and bending shape are displayed. It is also possible to display the amount of insertion section 4 inserted in the tube or the inserted depth, or the diameter of the tube and the bending state or position within the tube. The amount of insertion section 6 inserted in the tube may be detected by a potentiometer or the like and can be displayed in numeral. When the tube's diameter is constant, it may be input through a keyboard, etc. and displayed on TV monitor 140. With regard to displaying the bending state or position within the tube, the tube may be represented by a pseudo image and this image may be combined with a pseudo image of the distal end portion of insertion section 6. FIG. 22 illustrates a specific example of such image combination. "40" at the lower portion in FIG. 22 indicates the tube's diameter entered through a keyboard, "L5.5" on the right side of "40" indicates the inserted depth (mm), "R" above "40" indicates the bending direction, "30°" indicates the bending amount, and the pseudo image at the top indicates the bending state of insertion section 6 within the tube.

What is claimed is:

1. An endoscope with an operating section and insertion section having a bending section, comprising:
   a bending member, formed of a shape memorizable alloy and disposed in said bending section of said insertion section, for bending said bending section;
   a power supply unit connected to said bending member;
   detecting means for detecting an amount of deformation of said bending member; and
   display means for displaying said amount of deformation of said bending member;
   wherein said detecting means comprises a conductive rubber mounted on said bending section.

2. The endoscope according to claim 1, wherein said display means includes a unit for converting said amount of deformation detected by said detecting means into a bent angle measurement, and a cathode ray tube for displaying said bent angle measurement.

3. An endoscope with an operating section and insertion section having a bending section comprising:
   a first bending member, formed of a shape memorizable alloy and disposed in said bending section of said insertion section, for bending said bending section;
   a power supply unit connected to said first bending member; and
   display means, including a second bending member that deforms at the same time as said first bending member, for displaying an amount of deformation of said bending section.

4. The endoscope according to claim 3, wherein said second bending member is connected in series to said first bending member.

5. The endoscope according to claim 3, wherein said second bending member is disposed within said operating section and is covered by a transparent cover for external visual confirmation.

6. The endoscope according to claim 3, further comprising an operating lever mounted with said second bending member, for manipulating said bending section.

* * * * *

UNITED STATES PATENT AND TRADEMARK OFFICE
CERTIFICATE OF CORRECTION

PATENT NO. : 4,899,731

DATED : February 13, 1990

INVENTOR(S) : TAKAYAMA et al

It is certified that error appears in the above-identified patent and that said Letters Patent is hereby corrected as shown below:

On the title page, under "Foreign Application Priority Data", the Japanese application "61-2760089" should read --61-276089--.

Signed and Sealed this

Twenty-sixth Day of March, 1991

*Attest:*

HARRY F. MANBECK, JR.

*Attesting Officer*        *Commissioner of Patents and Trademarks*